United States Patent [19]

Brown

[11] Patent Number: 5,057,604
[45] Date of Patent: Oct. 15, 1991

[54] NOVEL MONOCLONAL ANTIBODIES
[75] Inventor: Eric J. Brown, St. Louis, Mo.
[73] Assignee: Washington University, St. Louis, Mo.
[21] Appl. No.: 227,972
[22] Filed: Aug. 3, 1988
[51] Int. Cl.$^5$ .......................... C07K 13/00; C12N 5/00
[52] U.S. Cl. ................................. 530/387; 435/240.26
[58] Field of Search ........................................ 530/387

[56] References Cited
PUBLICATIONS

Hynes, Cell 48, 549–554 (1987).
Hemler et al., J. Biol. Chem. 262, 3300–3309 (1987).
Ginsberg et al., Thromb. Hemostasis, 59, 1–6 (1988).
Anderson & Springer, Ann. Rev. Med. 38, 175–194 (1987).
Brown & Goodwin, J. Exp. Med. 167, 777–793 (1988).
Wright & Meyer, J. Exp. Med. 162, 762–767 (1985).
Pierschbacher, Science, 238, 491–497 (1987).

Primary Examiner—Johann Richter
Attorney, Agent, or Firm—Scott J. Meyer; James W. Williams, Jr.

[57] ABSTRACT

A monoclonal antibody which specifically reconizes a receptor that binds to proteins that contain the amino acid sequence Arg-Gly-Asp which on binding said proteins causes the cells to become substantially more phagocytic.

1 Claim, 8 Drawing Sheets

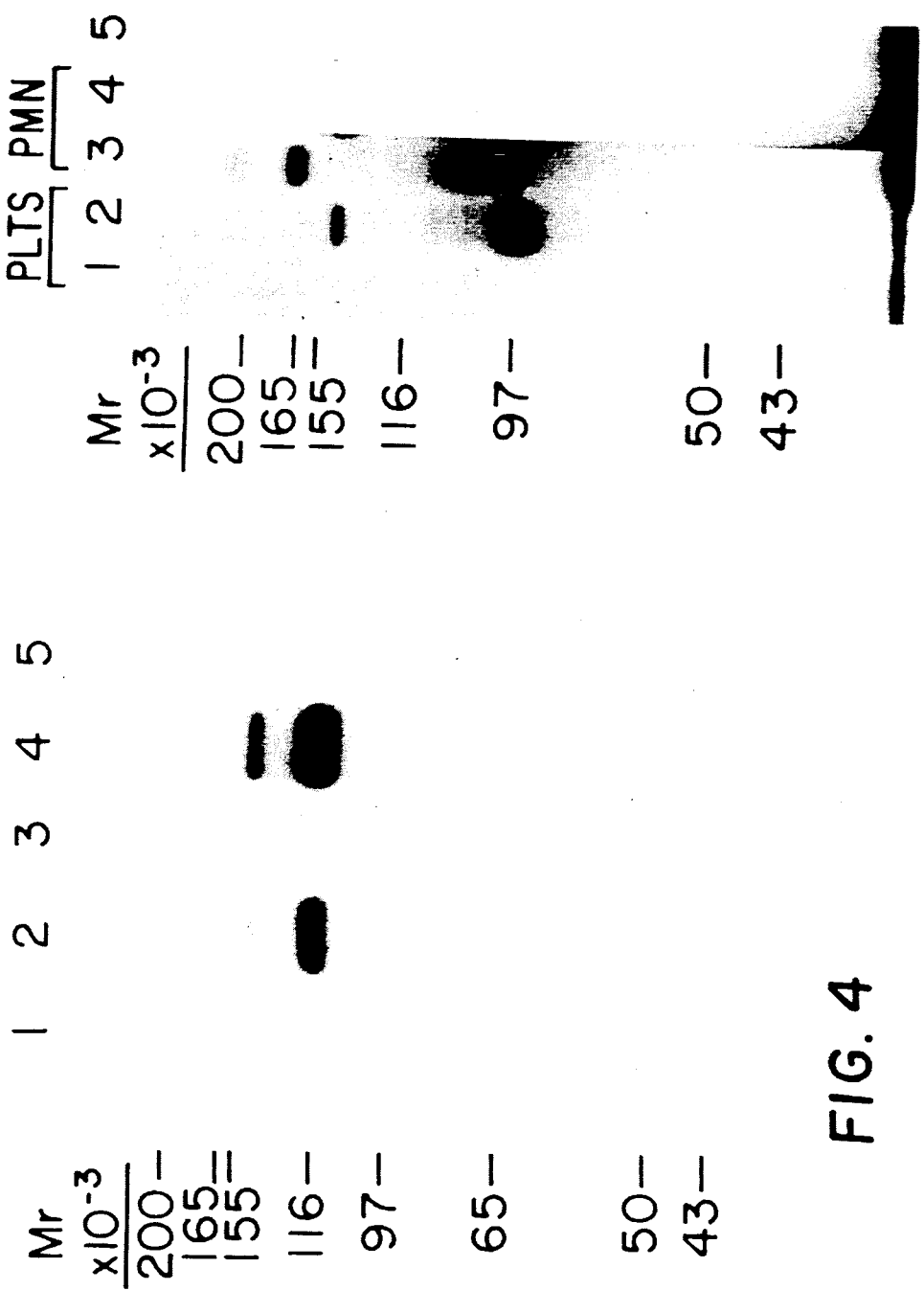

NOVEL MONOCLONAL ANTIBODIES

BACKGROUND OF THE INVENTION

The invention relates to novel monoclonal antibodies and, more particularly, to monoclonal antibodies specific to a unique integrin receptor.

The integrin superfamily of adhesive receptors are transmembrane heterodimeric molecules which function in cell-matrix and cell-cell adhesion [Hynes, *Cell* 48, 549-554 (1987)]. They are thought to function in adhesion processes by serving as transmembrane links between the extracellular environment and the cytoskeleton. As such they are intimately involved in many complex cell processes including thrombosis, hemostasis, cell maturation, embryogenesis, lymphocyte killing and phagocytosis. The integrins can be roughly classified into three groups: (1) VLA, the very late antigens first described on T lymphocytes, including the fibronectin receptor from human placenta and osteosarcoma cells [Hemler et al., *J. Biol. Chem.* 262, 3300-3309 (1987)]; (2) cytoadhesins, including the platelet gp IIb-/IIIa and the vitronectin receptor [Ginsberg et al., *Thromb. Hemostas.* 59, 1-6 (1988)]; and (3) LFA-1, Mac-1, p150,95, leukocyte-specific adhesion receptors, including the complement receptor for C3bi (CR3) [Anderson and Springer, *Ann. Rev. Med.* (1987)]. The heterodimers in each group are comprised of distinct alpha chains non-covalently linked to a common beta chain. Because of this, monoclonal antibodies to the beta chain of each group can be used to classify new receptors as membranes of one or another group within the integrins. As an example, the fibronectin receptor was shown to be a member of the VLA group because it bound A-1A5, a monoclonal antibody which recognizes all VLA beta chains.

In addition to significant structural and sequence homology, the integrins also exhibit ligand-binding similarities. Several of these receptors were first discovered because of their binding to extracellular matrix proteins via an Arg-Gly-Asp (RGD) amino acid sequence in the matrix ligands. The RGD-binding proteins of human neutrophils (PMN) and monocytes has been characterized by affinity chromatography of cell lysates on RGD-Sepharose ® [Brown and Goodwin, *J. Exp. Med.* 167, 777-793 (1988)]. It was shown that both phagocytes express a heterodimeric receptor distinct from the LFA-1, Mac-1, p150,95 family which exhibits immunological cross-reactivity with gp IIb/IIIa on platelets. Phagocytes undergo a number of important functional changes during recruitment to an inflammatory or infected site. These include changes in the receptors expressed at the plasma membrane, activation of new metabolic pathways, increases in oxygen consumption and the production of reactive oxygen metabolites, and augmentation of phagocytosis. Extracellular matrix proteins have been shown to mediate some of these physiologic changes, especially enhancement of ingestion of opsonized particles by monocytes and macrophages. This enhancement is dependent on recognition of the RGD sequence within these matrix proteins [Brown and Goodwin, supra; Wright and Meyer, *J. Exp. Med.* 162, 762-767 (1985)]. It is hypothesized that the molecule identified by affinity chromatography on RGD-Sepharose might be the phagocyte receptor involved in extracellular matrix-stimulated ingestion.

For further background information on the RGD sequence and integrins, see Ruoslahti and Pierschbacher, *Science* 238, 491-497 (1987).

BRIEF DESCRIPTION OF THE INVENTION

In accordance with the present invention novel monoclonal antibodies to a unique integrin receptor are provided. In particular, a monoclonal antibody has been prepared which specifically recognizes a receptor that binds to proteins that contain the amino acid sequence Arg-Gly-Asp (RGD) which on binding said proteins causes the cells to become substantially more phagocytic.

A preferred monoclonal antibody having the foregoing characteristics, designated herein as B6H12, recognizes an antigen on human polymorphonuclear leukocytes (neutrophils - PMN) distinct from any other previously described integrin. It inhibits RGD-mediated phagocytosis enhancement and has a broad specificity for RGD-containing proteins. This novel monoclonal antibody inhibits both RGD-dependant ligand binding and extracellular matrix-stimulated ingestion by human PMN. Ligand binding by this novel integrin receptor is rapidly lost upon activation of the myeloperoxidase (MPO)-$H_2O_2$-halide system in PMN, thereby suggesting that this receptor is important early in the inflammatory response of PMN, before significant respiratory burst or degranulation occur.

An isolate of the hybridoma cells for production of monoclonal antibody B6H12 is on deposit with the American Type Culture Colection, Rockville, Maryland, under accession number ATCC HB 9771.

DETAILED DESCRIPTION OF THE INVENTION

Figure 1:
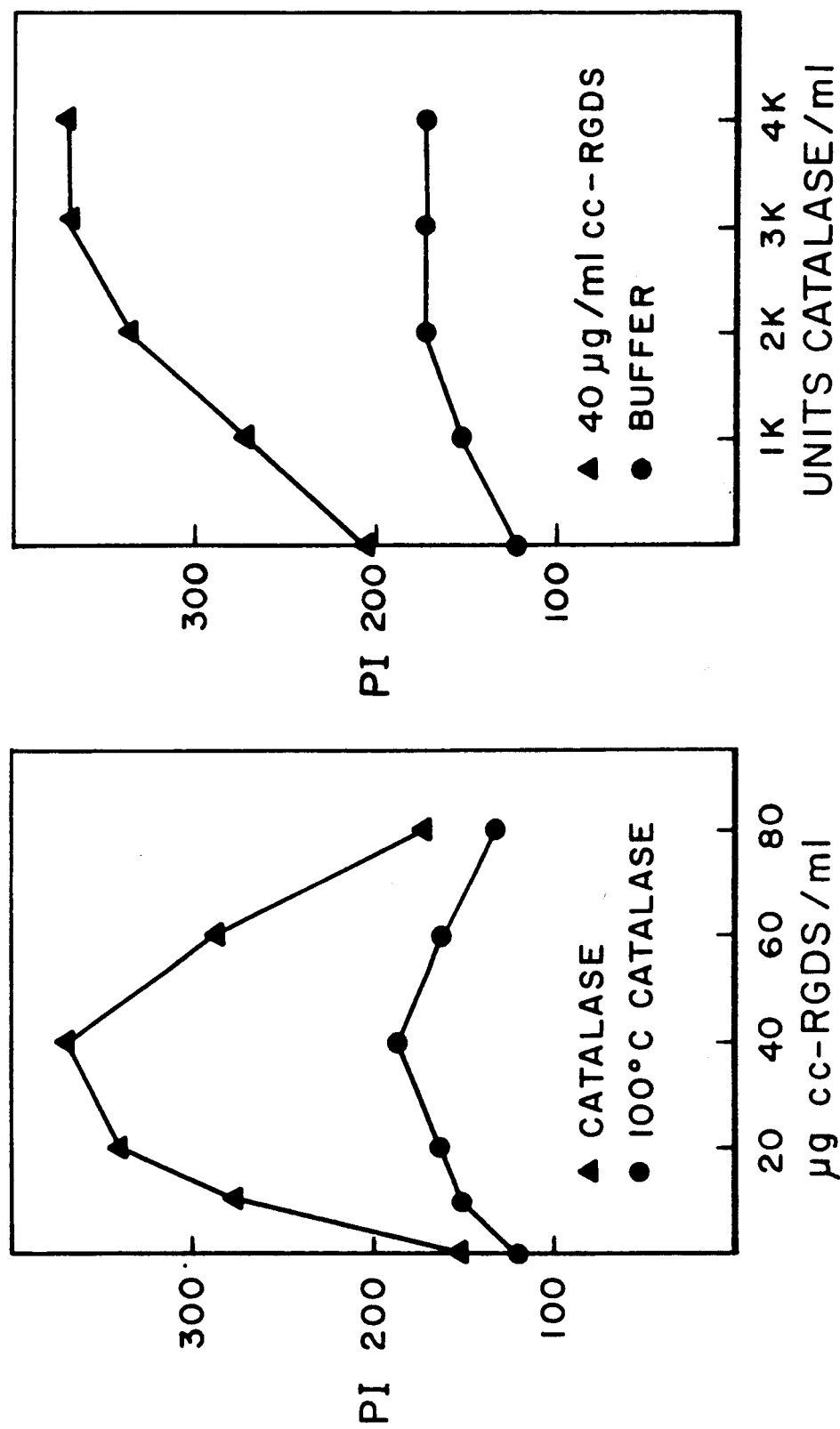

While the speoification concludes with claims particularly pointing ou and distinctly claiming the subject matter regarded as forming the present invention, it is believed that the invention will be better understood from the following detailed description of preferred embodiments taken in conjunction with the accompanying drawings, in which:

FIG. 1 is a graphical representation which shows the effect of catalase on cytochrome c-RGDS-stimulated ingestion of IgG-opsonized sheep erythrocytes (EIgG). (A). PMN and EIgG were incubated with the final concentrations of cc-RGDS (20, 40, 60, or 80 μg/ml) in the presence of either 5000 (5K) units/ml of native catalase (Δ) or catalase heated at 100° C. for 10 min (●). After 30 min at 37° C., phagocytosis was assessed as a phagocytic index, the number of EIgG ingested/100 PMN (PI). (B). PMN and EIgG were incubated with increasinq concentrations of catalase in the presence (Δ) or absence (●) of 40 μg/ml of cytochrome c-RGDS (cc-RGDS). After 30 min at 37° C., phagocytosis was assessed as a PI.

Figure 2:
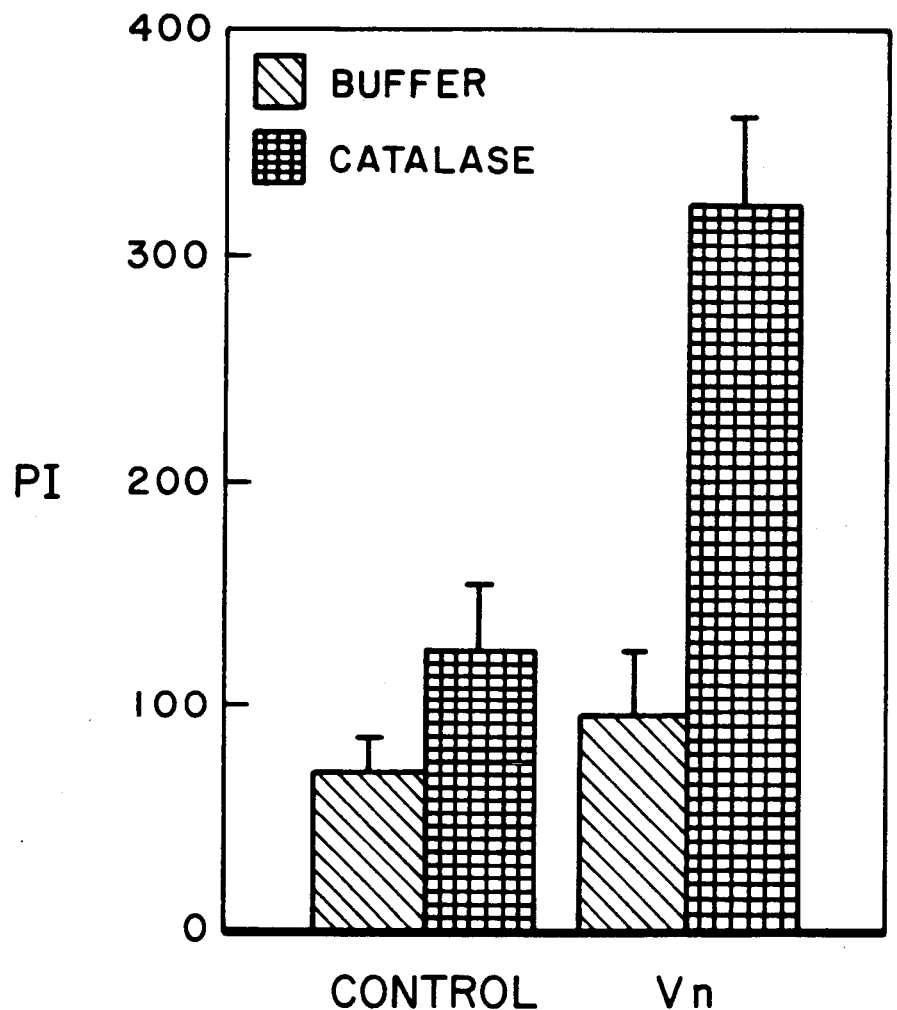

FIG. 2 is a graphical representation which shows the effect of catalase on ingestion of EIgG by PMN adherent to control or vitronectin-coated surfaces. Plastic Lab-Tek chambers were coated with either carbonate buffer, pH 9.6 (control) or 10 μg/ml of vitronectin in carbonate buffer (Vn) for 2 hrs at 37° C. After washing the chambers, PMN ($2.5 \times 10^4$/well) were adhered in the presence or absence of 5K units/ml catalase for 45 min at 37° C. Catalase was removed by extensive washing. The EIgG were added and phagocytosis assessed as a PI after 30 min at 37° C.

Figure 3B:
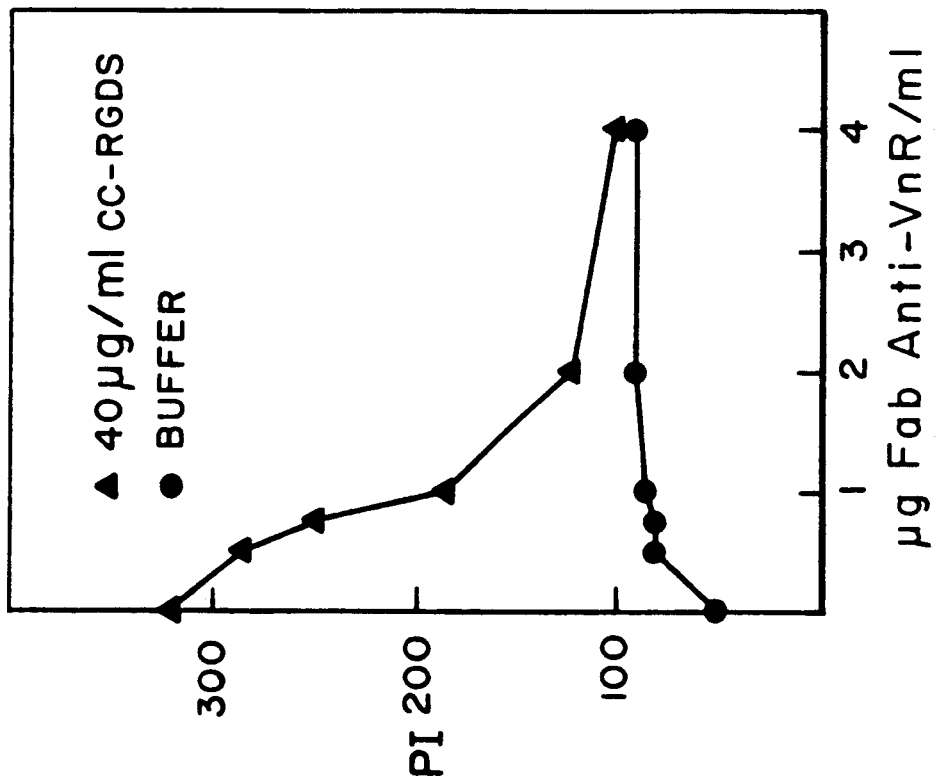

FIG. 3 is a graphical representation which shows the effect of mAB B6H12 and polyclonal Fab anti-vitronectin receptor (VnR) on cc-RGDS-stimulated ingestion of EIgG. PMN were incubated with the indicated concentrations of either mAB B6H12 (A) or polyclonal anti-VnR (B) for 15 min at room temperature. Without washing, the EIgG were added and the mixture incubated with (△) or without (●) 40 μg/ml of cc-RGDS. After 30 min at 37° C. phagocytosis was assessed as a PI.

FIG. 4 shows the immunoprecipitation from surface-labelled PMN with mAB B6H12 or polyclonal anti-vitronectin receptor. Surface-iodinated PMN lysates were immunoprecipitated with the following antibodies: lane 1, pre-immune rabbit serum; lane 2, rabbit polyclonal anti-VnR; lane 3, mAB 7G2 (anti-VnR beta chain); lane 4, mAb B6H12; and lane 5, mAB B3F12 (anti-VnR). The immunoprecipitates were analyzed under reducing conditions, 50 mM dithiothreitol (DTT), by sodium dodecylsulfate polyacrylamide gel electrophoresis (SDS-PAGE).

FIG. 5 shows the immunoprecipitation from surface-labelled platelets and PMN with mAb B6H12 and mAB 7G2. Surface-iodinated platelets (lanes 1 & 2) and PMN (lanes 3-5) were immunoprecipitated with the following antibodies: lanes 1 and 3, mAB B6H12; lane 2, mAB 7G2; and lanes 4 and 5, mAB B3F12. The precipitates were analyzed under non-reducing conditions by SDS-PAGE.

Figure 6A:
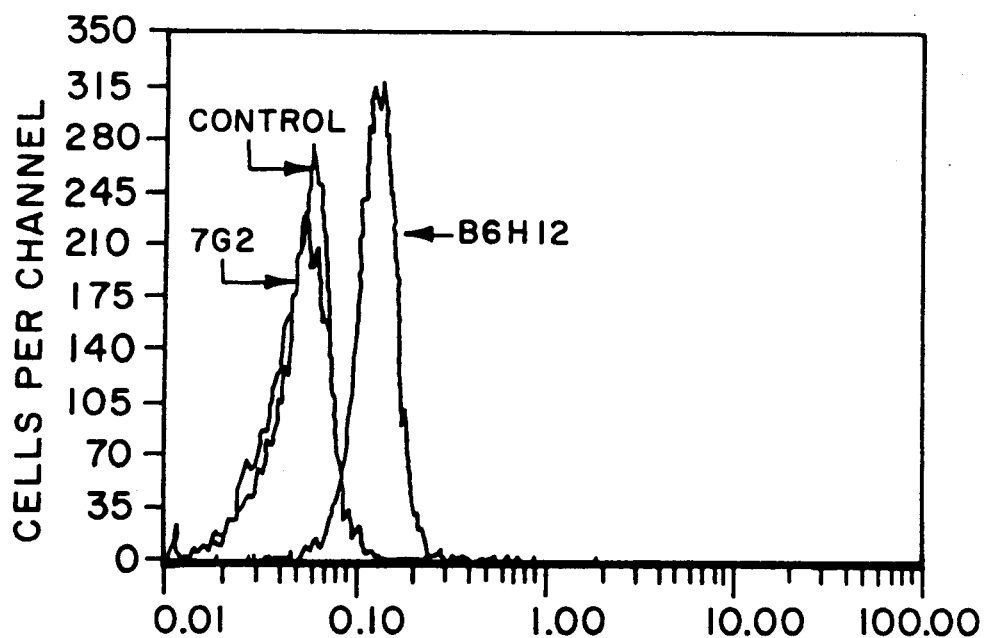
Figure 6B:
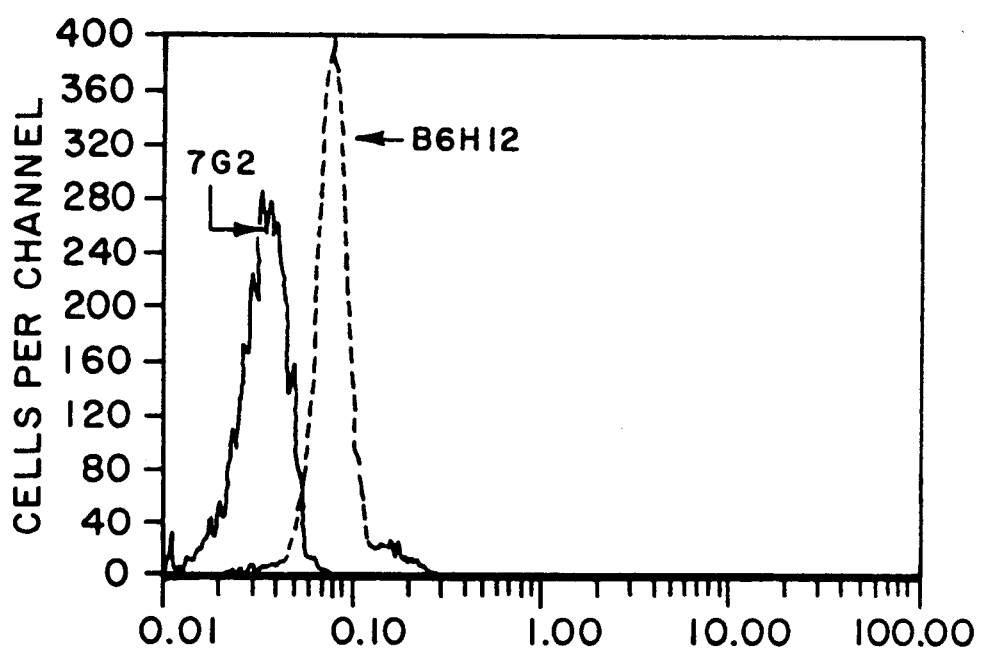

FIG. 6 is a graphical representation which shows the mAb B6H12 profile of normal and leukocyte adhesion deficient (LAD) PMN as analyzed by Fluorescence Activated Cell Sorter (FACS). Normal PMN (A) and LAD PMN (B) were analyzed by indirect immunofluorescence for mAb B6H12. Both normal and LAD PMN express the B6H12 antigen. LAD PMN are unable to express the Mac-1, LFA-1, P150,95 because of an abnormality in beta chain synthesis.

FIG. 7 is a graphical representation which shows that fibronectin (Fn) and its cell-binding domain (CBD) stimulate ingestion of EIgG in a manner dependent on B6H12 antigen. (A & B). PMN were incubated with 5K units/ml catalase and a 1:20 dilution of tissue culture supernatant containing either mAB B6H12 (●) or mAB B3F12 (△) for 15 min at room temp. Without washing, the EIgG were added and the mixture incubated with either increasing concentrations of Fn (A), increasing concentrations of its purified CBD (B), or 40 μg/ml cc-RGDS (open symbols) (A & B). After 30 min at 37° C., phagocytosis was assessed. (C). Fn (5 g/ml) or buffer were incubated with either buffer, mAB's Fn5, Fn8, or HFn7.1 at 10 μg/ml for 30 min at room temp. PMN, 5K units/ml catalase, and EIgG were added and phagocytosis assessed as a PI after 30 min at 37° C.

Figure 8B:
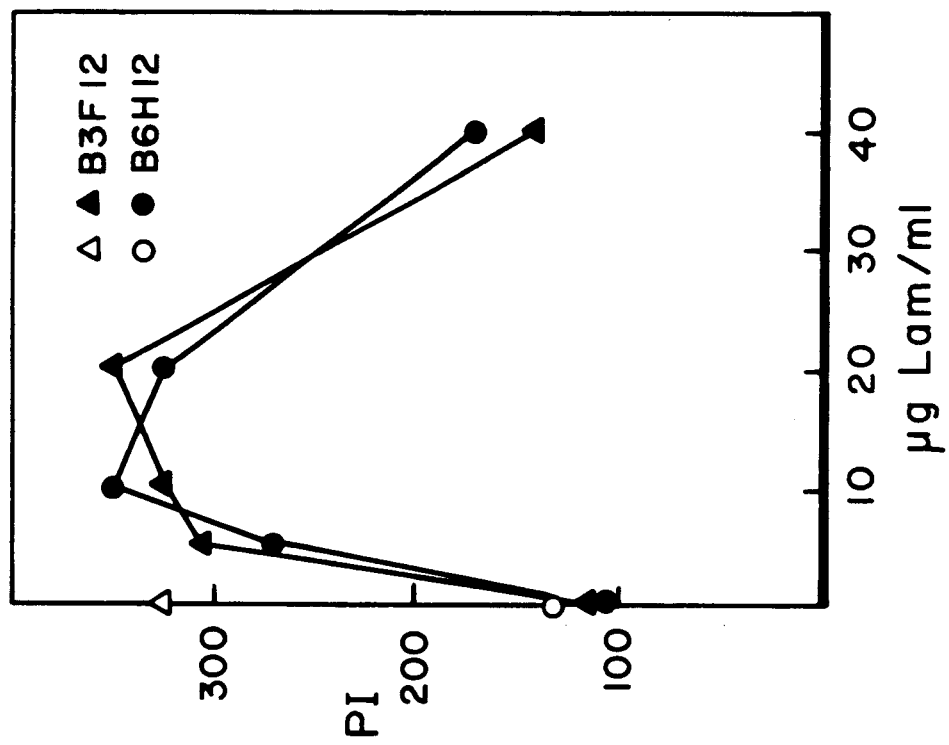

FIG. 8 is a graphical representation which shows the effect of mAB B6H12 on collagen type IV-and lamin-stimulated ingestion of EIgG. (A & B). PMN and 5K units/ml of catalase were incubated with a 1:20 dilution of tissue culture supernatant containing either mAB B3F12 (△) or mAB B6H12 (●) for 15 min at room temp. Without washing, the EIgG were added and the mixture incubated with either increasing concentrations of collagen type IV (A), increasing concentrations of lamin (B), or 40 μg/ml of cc-RGDS (open symbols) (A & B). After 30 min at 37° C., phagocytosis was assessed as a PI.

Figure 9C:
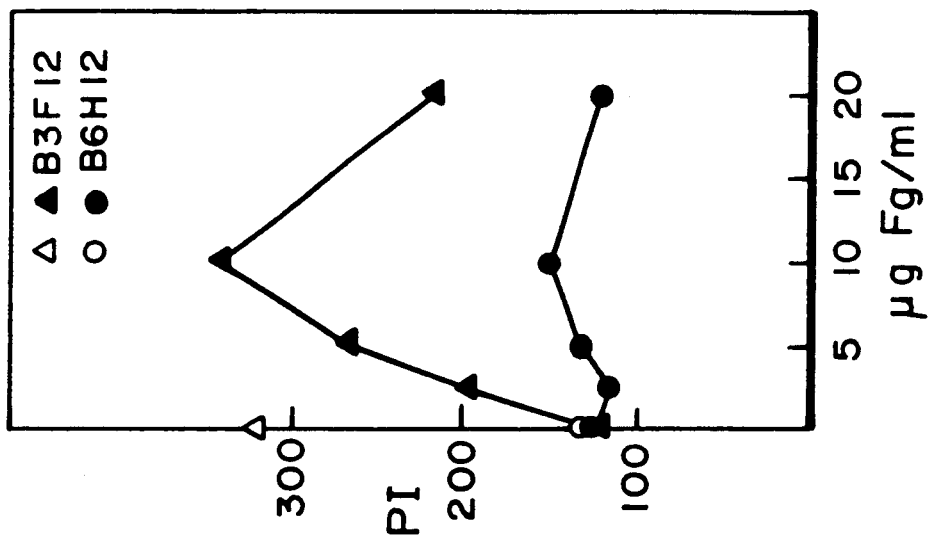
Figure 9B:
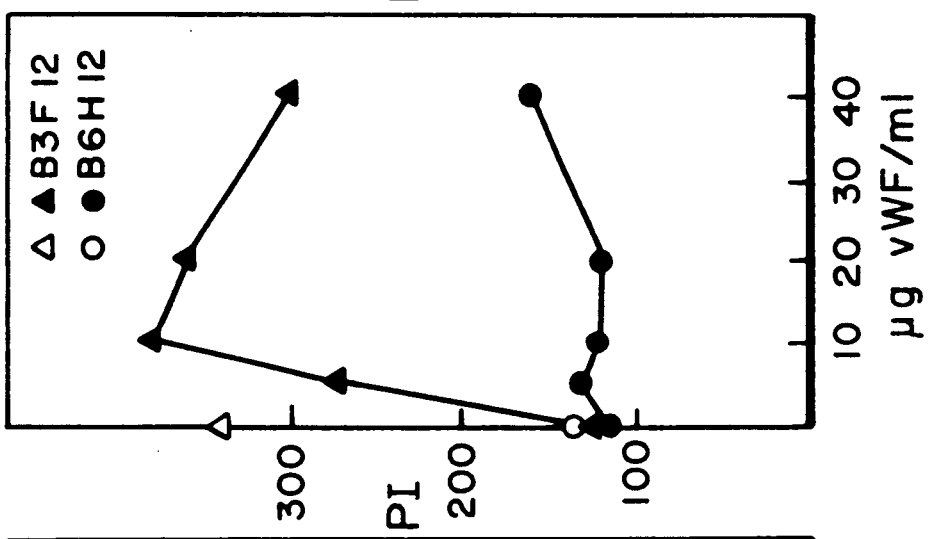
Figure 9A:
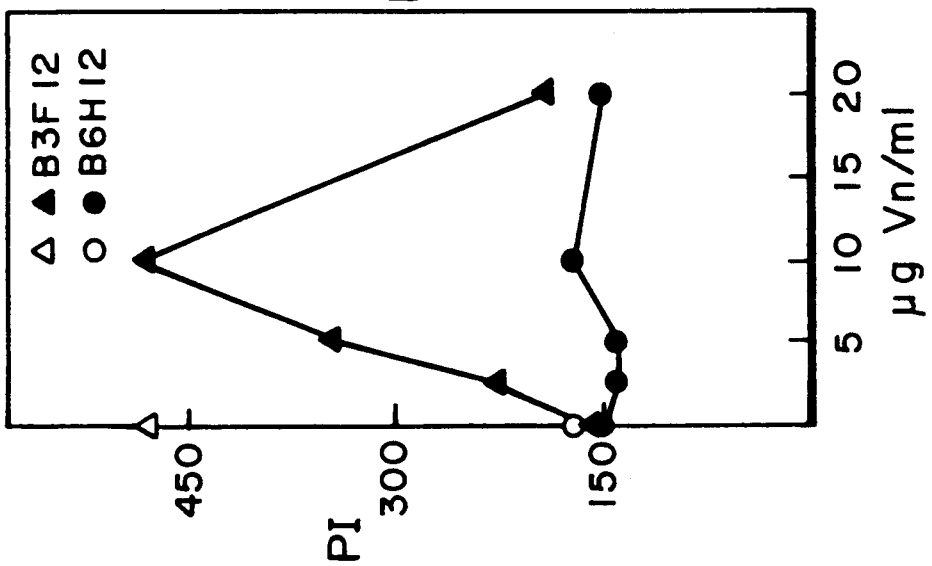

FIG. 9 is a graphical representation which shows the effect of mAb B6H12 on vitronectin (Vn)-, von Willebrand's factor (vWF)-, and fibrinogen (Fg)-stimulated ingestion of EIgG. (A-C). PMN and 5K units/ml catalase were incubated with a 1:20 dilution of tissue culture supernatant containing mAb B3F12(△) or mAb B6H12 (●) for 15 min at room temp. Without washing, the EIgG were added and the mixture incubated with either increasing concentrations of Vn (A), increasing concentrations of vWF (B), increasing concentrations of Fg (C), or 40 μg/ml of cc-RGDS (open symbols) (A-C). After 30 min at 37° C., phagocytosis was assessed as a PI.

The production of monoclonal antibodies having the characteristics of B6H12 as described herein can be carried out by conventional procedures such as described, for example, by Köhler and Milstein, Nature 256, 495-497 (1975; Eur. J. Immunol. 6, 511-519 (1976). According to this method, tissue-culture adapted mouse myeloma cells are fused to spleen cells from immunized mice to obtain the hybrid cells that produce large amounts of a single antibody molecule. In this procedure, human placental vitronectin receptor protein was used as the immunogen. This protein antigen is sufficiently large so that no hapten is necessary for immunogenicity.

A suitable mouse myeloma cell line for use in making these antibodies is the Sp2/0-Ag14 cell line. This is a well-known cell line of BALB/c origin defined by Schulman, Wilde and Köhler, Nature 276, 269-270 (1978). These cells, which do not synthesize Ig chains, can be obtained from the Basel Institute for Immunology and are available to the public from the American Type Culture Collection, Rockville, Md., under accession number ATCC CRL-1581. A preferred mouse myeloma cell line which also is a non-secretor cell line of BALB/c origin is P3-X63-Ag8.653 [Kearney et al., J. Immunol. 123, 1548-1550 (1979)]. A preferred method of carrying out the fusion of the myeloma cells and the spleen cells is by the conventional general procedure described by Galfre et al., Nature 266, 550-552 (1977). This method employs polyethylene glycol (PEG) as the fusing agent for the cells growing as monolayers, followed by selection in HAT medium (hypoxanthine, aminopterin and thymidine) as described by Littlefield, Science 145, 709-710 (1964).

Further background information on suitable methodology for producing monoclonal antibodies can be had by reference to texts in the field, for example, Goding, "Monoclonal Antibodies: Principles and Practice," Academic Press, N.Y., 1983.

It will be appreciated that not all hybridomas prepared as described herein will have optimum antibody activity. As is customary in this field, radioimmunoassay and enzyme immunoassay procedured can be readily used to screen the population of hybridomas for individual clones which secrete optimum specificity. The radioimmunoassay is based upon the competition between radiolabeled and unlabeled antigen for a given amount of antibody which can be determined by conventional general procedure as described, for example, by Yalow et al. J. Clin. Invest. 39, 1157 (1960). In the enzyme immunoassay such as ELISA, the revealing agent is conjugated with an enzyme instead of $^{125}I$. After washing away any unbound material, the bound enzyme is revealed by addition of a substrate which undergoes a color change. See, e.g., Engvall and Perlmann, Immunochemistry 8, 871-874 (1971); J. Immunol. 109, 129-135 (1972).

The following detailed Example will further illustrate the invention although it will be appreciated that the invention is not limited to this Example or the specific details presented therein. In this Example, detailed test procedures were carried out to provide the data and results shown in the accompanying FIGS. 1 to 9 and in Tables 1 and 2, below, with respect to the preferred monoclonal antibody B6H12.

EXAMPLE

Special Reagents

The following reagents were purchased from Sigma Chemical Co., St. Louis, Mo.: chicken egg albumin (ovalbumin), catalase (bovine liver, 52,000 U/mg), cytochrome c (Type XIV, pigeon heart), and fibrinogen. A 10 x concentrated stock of Hank's Balanced Salt Solution (HBSS) was purchased from GIBCO, Grand Island, N.Y. Human vitronectin was purchased from Calbiochem-Behring Corp., La Jolla, Calif. Human fibronectin and the chymotryptic cell-binding domain of 105–110 kd were purified as described by Bohnsack et al., *J. Immunol.* 136, 3793 (1986). Collagen type IV and laminin were obtained from Dr. Hynda Kleinmann, National Institute of Dental Research, Bethesda, Md. von Willebrand's Factor (vWF) was obtained from Dr. Sam Santoro, Washington University, St. Louis, Mo. The synthetic peptide Lys-Tyr-Ala-Val-Thr-Gly-Arg-Gly-Asp-Ser (KYAVTGRGDS) was obtained from Dr. Steven Adams, Monsanto Company, St. Louis, Mo. Peptides GRGDSC or GDGDSC or amino acid Cys (C) as a control was linked to cytochrome c via bromacetyl succinamide [(Bernatowicz and Matsueda, *Anal Biochem.* 155, 95–102 (1986)].

Purification of Rgd Binding Proteins From Human Placenta

Membranes were isolated from fresh human placenta, processed and solubilized as described by Calderon et al., *Proc. Natl. Acad. Sci. U.S.A.* 85, 4837–4841 (1988)]. Protein was incubated with wheat germ agglutinin and adherent proteins eluted with 0.5M N-acetylglucosamine (GlcNAc) in a 0.5M NaCl, 0.05M phosphate, pH 7.4, buffer containing phenyl methyl sulfonyl fluoride, iodocetamide and 50 mM octylglucoside. The eluate was dialyzed to remove the GlcNAc and applied to a γ-IFN-Sepharose column. Unbound protein was washed through with octylglucoside-containing buffer and applied to a column bearing decapeptide KYAVTGRGDS. Bound proteins were eluted by EDTA (Brown and Goodwin, supra). SDS PAGE analysis showed only two Coomasie stained bands which had $M_r$ on both unreduced and reduced gels consistent in the vitronectin receptor.

Monoclonal and polyclonal antibodies mAB A1A5 tissue culture supernatant was obtained from Dr. Martin Hemler, Boston, Mass. Goat polyclonal anti-fibronectin receptor (VLA-5) was obtained from Dr. Rudolph Juliano, Chapel Hill, N.C. Polyclonal antibody to purified VnR was produced in rabbits. The IgG was isolated from serum by caprylic acid precipitation and DEAE chromatography [Steinbuch and Audran, *Arch. Biochem. Biophys.* 134, 279–284 (1969)]. Fab fragments were prepared by papain digestion. Monoclonal antibodies were produced by immunization of BALB/c mice with purified VnR. Spleen cells were fused with the nonsecreting myeloma cell line P3X63AG8.6.5.3. Hybridoma culture supernatants were screened for antibodies reactive with purified VnR by ELISA. Reactive antibodies were screened further for binding to PMN by indirect immunofluorescent staining and fluorescence flow cytometry. Antibodies 7G2, B3F12, 6H12, and 3F12 were reactive with purified VnR by ELISA but unreactive with PMN. These mAB also immunoprecipitated VnR from detergent solubilized placental membrane preparations. mAb 7G2 reacted with the VnR beta-chain by Western blot but none of the others reacted on Western blots, suggesting that they recognized conformational epitopes on VnR. mAb B6H12 was reactive both with purified VnR by ELISA and with PMN by fluorescence flow cytometry. Antibodies were produced in the form of tissue culture supernatant or ascites in pristane-primed mice for further characterization. IgG was purified from ascites by caprylic acid precipitation and DEAE chromatography (Steinbuch and Audran, supra).

Isolation of PMN

PMN were isolated from heparinized blood from normal human volunteers and from a single patient with leukocyte adhesion deficiency (LAD) by the method of Boyum, *J. Clin. Lab. Invest.* 21 (Supp. 97), 77–89 (1968) with modifications of Gresham et al., *J. Immunol.* 139, 4159–4166 (1987). In some tests the erythrocyte lysis step was omitted to prevent possible damaqe to the PMN during the hypotonic lysis procedure.

Immunoprecipitation and SDS-PAGE Analysis

For cell-surface labelling, $30-100 \times 10^6$ PMN were iodinated by chloroglycoluril [Markwell and Fox, *Biochemistry* 17, 4807–4817 (1978)] in the presence of 25 μM p-nitrophenyl p'-guanidino-benzoate (NPGB) and 0.5% $NaN_3$ for 30 min at 0° C. Cells were solubilized in HEPES buffer containing 200 mM octylglucoside, 20 mM iodoacetamine, 2 μM pepstatin, 2 μM leupeptin, 25 μM NPGB, 1 mM $CaCl_2$, and 1 mM $MgCl_2$, pH 7.4. Total placental membrane proteins were labelled with $^{125}I$ using chloroglycoluril after detergent solubilization. Protein-bound and free iodide were separated on Sephadex G-25 columns. Aliquots of labelled proteins were incubated with monoclonal or polyclonal antibodies for 2 hours (h) at 4° C. and then for a further 1 h with either anti-mouse Ig Sepharose (Cooper Biomedical, Malvern, Pa.) or Protein A Sepharose (Pharmacia, Piscataway, N.J.), respectively. Immunoprecipitates were analyzed on 6% SDS-polyacrylamide gels and autoradiography performed as described by Maizel, *Meth. Virol.* 5, 179–246 (1971).

Opsonization of Sheep Erythrocytes

Sheep erythrocytes (E) were purchased from Whittaker M.A. Bioproducts, Walkersville, Md. EIgG were prepared as described by Gresham et al, supra, using a 1/500 dilution of rabbit IgG anti-E (Diamedix, Miami, Fla.).

Phagocytosis assay

PMN phagocytosis was assessed by a fluid-phase assay as described by Gresham et al., supra; Gresham et al., *J. Clin. Invest.*, In press (1988). PMN were suspended in HBSS containing 4.2 mM $NaHCO_3$, 10 mM HEPES, 1.5 mM $CaCl_2$, 1.5 mM $MgCl_2$, and 1% ovalbumin, pH 7.4 (HBSS++-1% OVA). The reaction mixtures contained $1.0 \times 10^5$ PMN, the indicated antibody oonoentrations, the indicated stimulatory ligands, 5K units/ml catalase, and 15 μl of EIgG ($5.0 \times 10^8$/ml) in a final volume of 115 μl. The assay tubes were incubated at 37° C. in 5% $CO_2$ for 30 min. The non-ingested E were lysed with 0.83% ammonium chloride. Phagocytosis was assessed by light microscopy and quantitated as a phagocytic index (PI), the number of EIgG ingested/100 PMN).

Cytochrome c-RGDS Binding Assay

Cytochrome c-RGDS was radioiodinated by chloroglycoluril [Markwell and Fox, *Biochemistry* 17, 4807–4817 (1978)] for 15 min at 0° C. PMN ($5.0 \times 10^5$) in HBSS++-1% OVA were incubated with 10 μg of radiolabelled cc-RGDS in the presence of 5K U/ml of catalase and 293 μg of unlabelled cc-C in a final volume of 250 μl. The reaction mixtures were incubated in 1.5 ml Eppendorf tubes for 30 min at 37° C. The mixtures were overlayered on Versilube (General Electric) and centrifuged at 12,000 ×g to assess pellet associated radioactivity. Specific binding was determined by subtracting the radioactivity bound in the presence of 293 g of unlabelled cc-RGDS from the total radioactivity. Unlabelled cc-C was included in the reaction to control for any binding due to cytochrome c and not specifically due to the RGDS moiety. For inhibition tests, the various inhibitors were included in the reaction at the indicated concentrations. Antibodies were incubated with the PMN at the indicated concentrations for 15 min at room temperature prior to the addition of the other reactants.

Fluorescence flow cytometry

PMN ($1.0 \times 10^6$) were stained with excess murine mAbs and FITC F(ab')$_2$anti-mouse Ig (Tago, Inc., Burlingame, Calif.) at 0° C. After washing with phosphate buffered saline (PBS), the cells were resuspended in 0.3 ml 0.5% paraformaldehyde in PBS prior to analysis on a FACS IV (Becton-Dickinson, Sunnyvale, Calif.).

The results of the foregoing detailed test procedures are further tabulated in Tables 1 and 2, below.

TABLE 1

| Effect of catalase on cc-RGDS binding RGDS-specific cpm's bound/$10^6$ PMN[a] | |
|---|---|
| +catalase | 30,267 ± 1,930 SEM, n = 10 |
| −catalase | 3,394 ± 931 SEM, n = 5 |

[a]PMN ($1.0 \times 10^6$) were incubated with 40 μg of $^{125}$I-cc-RGDS in the presence (+) or absence (−) of 5,000 units of catalase in 1 ml for 30 min at 37° C. The PMN were centrifuged through oil and the pellet-associated counts assessed. Specific binding was calculated as described in the detailed test procedures, above.

TABLE 2

| Inhibition of cc-RGDS specific binding to PMN | | |
|---|---|---|
| | cc-RGDS specific cpm's/$10^6$ PMN[a] | % I[b] |
| cc-C (1.16 mg/ml) | 30,173 ± 1,748 n = 11 | 0 |
| GRGDSC (500 ug/ml) | 6,144 ± 2,905, n = 3 | 79.6% |
| peptide 32 (500 μg/ml) | 39,442 ± 7,800, n = 2 | 0 |
| Fn (500 μg/ml) | 7,106 ± 3,568, n = 3 | 76.5% |
| Fab anti-VnR (4 μg/ml) | 1,312 ± 867, n = 5 | 95.7% |
| B6H12 (4 μg/ml) | 1,877 ± 1,811, n = 3 | 93.8% |
| B3F12 (4 μg/ml) | 27,948 ± 5,701, n = 3 | 7.4% |

[a]PMN ($1.0 \times 10^6$) were incubated wth 40 μg of $^{125}$I-cc-RGDS with the indicated concentrations of unlabelled inhibitors in the presence of 5,000 units of catalase in 1 ml for 30 min at 37° C. The PMN were centrifuged through oil and the pellet-associated counts assessed. Specific binding was calcualted as described in the detailed test procedures, above.
[b]Calculated from the mean cpm's. Percent inhibition = 100 × (1-[mean cpm's in the presence of inhibitor]/[mean cpm's in the presence of cc-C]).

Explanation and significance of the foregoing results are as follows:

A. Catalase is required to demonstrate both cytochrome c-RGDS (cc-RGDS) binding and stimulation of PMN Fc receptor-mediated phagocytosis.

It is reported that while monocytes express both an integrin which binds to RGD-Sepharose and a structurally distinct integrin which binds preferentially to Sepharose bearing the fibronectin (Fn) cell binding domain (CDB), this is not the case for PMN. Instead, PMN express a single integrin-like receptor which binds preferentially to RGD-Sepharose columns (Brown and Goodwin, supra). Because this presented a simpler system for determination of the characterizations of the RGD-binding receptor involved in phagocytosis enhancement, it was decided to investigate extracellular matrix stimulation of PMN phagocytosis. Fibronectin has been reported to stimulate ingestion of C3b-opsonized sheep erythrocytes (EC3b) by fMLF- or C5a-stimulated PMN [Pommier et al., *J. Exp. Med.* 159, 137–151 (1984)] but not to stimulate the ingestion of IgG-opsonized E (EIgG) by PMN [Wright et al., *Ibid.* 158, 1338–1342 (1983)]. It was decided to avoid the added complication of chemotactic peptide stimulation of PMN, as the expression of other adhesive receptors (i.e. CR3) which bind ligand via an RGD sequence [Wright et al., *Proc. Natl. Acad. Sci. U.S.A.* 84, 1965–1968 (1987)] is markedly enhanced by these stimuli. It was therefore determined to investigate further the ability of extracellular matrix proteins to stimulate EIgG ingestion. Because many adhesive receptors are present on PMN, and matrix proteins such as Fn may interact with cell surfaces via several domains, a non-physiologic ligand was developed which would interact with PMN only by an RGD sequence. Either the hexapeptide GRGDSC or either GDGSC or the single amino acid C as controls was linked to pigeon heart cytochrome c via a bromacetyl succinamide linkage. The amino acid sequence for this cytochrome has been determined and does not contain an RGD sequence. These ligands are referred to as cc-RGDS, cc-DGDS, or cc-C and were used to assess RGDS-stimulated PMN Fc receptor-mediated phagocytosis. As shown in FIG. 1A, in the presence of catalase, cc-RGDS stimulated PMN ingestion of EIgG in a dose-dependent manner with an optimal concentration of 40 μg/ml. As with other stimuli that affect PMN Fc receptor-mediated ingestion, the dose response curve in biphasic [Gresham et al., *J. Immunol.* 139, 4159–4186 (1987)]. This clearly distinguishes the dose-response of RGDS stimulation on PMN from that on monocytes [Pommier et al., *J. Exp. Med.* 157, 1844–1856 (1983)]. In preliminary tests it was discovered that the inclusion of catalase was necessary to consistently observe cc-RGDS-stimulated ingestion (FIG. 1A). Ingestion performed in the presence of catalase incubated at 100° C. for 10 min was significantly reduced (FIG. 1A). cc-C or cc-DGDS up to concentrations of 80 μg/ml had no effect on EIgG ingestion even in the presence of catalase (data not shown). The effect of catalase on cc-RGDS-stimulated ingestion was dose-dependent (FIG. 1B). The inclusion of catalase also slightly enhanced non-stimulated ingestion of EIgG (FIG. 1B). This effect of catalase and inhibitors of the $H_2O_2$-MPO-halide system on PMN IgG Fc- and complement-mediated ingestion has been reported [Stendahl et al., *J. Clin. Invest.* 73, 366–373 (1984); Gaither et al., *Inflammation* 11, 211–227 (1987)]. In addition, the inclusion of either 10 mM $NaN_3$ (an inhibitor of MPO) or 10 mM methionine (a competitor for the damaging oxidant) also revealed consistent stimulation of ingestion by cc-RGDS. These data indicated that the MPO-hydrogen peroxide-halide system was generating an oxidant which damaged either some step in the pathway for RGD-mediated enhancement of phagocytosis or the receptor responsible for cc-RGDS-stimulated ingestion. To examine the latter possibility, the effect of catalase on binding of radiolabelled cc-RGDS to PMN was examined under the conditions of the phagocytosis assay. In the presence of catalase, a 9-fold increase in the amount of cc-RGDS bound was observed over the amount bound in the absence of catalase (Table 1). These data indicated that the effect of catalase was on the binding of the cc-RGDS ligand. To further examine this, the effect of catalase on EIgG ingestion by PMN adherent to solid-phase vitronectin was assessed. In this assay the catalase was present only during the adherence of the PMN and was washed away prior to the addition of the EIgG. Vitronectin contains an RGDS sequence and enhances monocyte ingestion of EC3b (Brown and Goodwin, supra). As shown in FIG. 2, even though catalase was present only during the adherence of the PMN to either the control or vitronectin-coated surface, it significantly enhanced vitronectin-stimulated ingestion of EIgG. These data and those in Table 1 indicated that the effect of catalase was on the interaction of the ligand with the PMN surface and not a general one on the phagocytic process. All subsequent assays were performed in the presence of catalase.

B. mAB B6H12 and polyclonal Fab anti-vitronectin receptor (VnR) inhibit both cc-RGDS binding and RGD-stimulated phagocytosis.

Figure 3A:
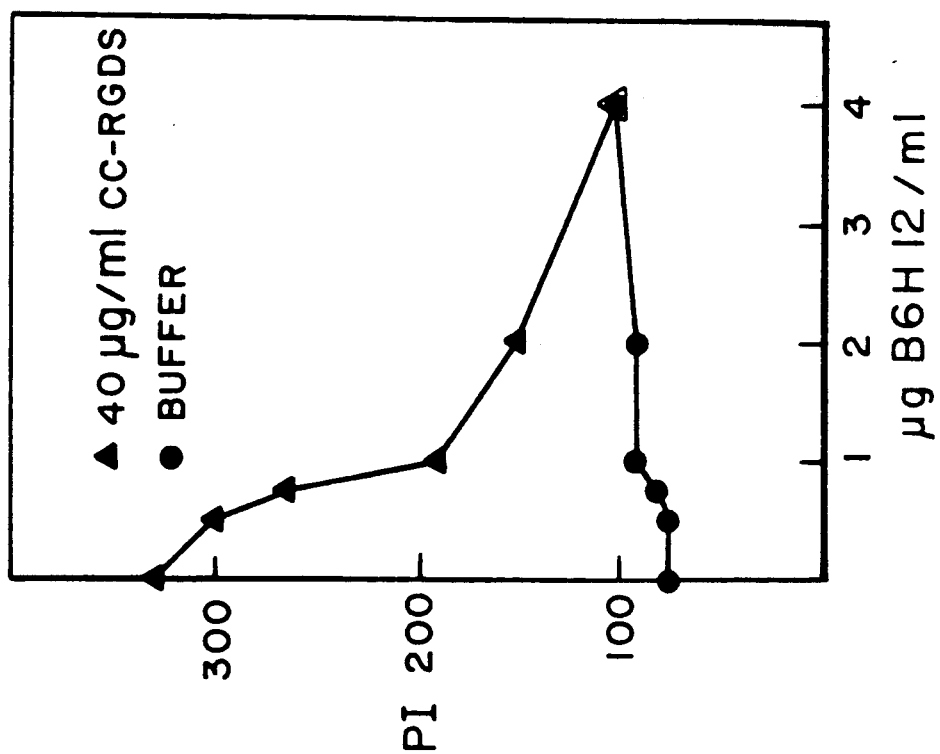

To facilitate isolation of the extracellular matrix receptor involved in phagocytosis enhancement, a polyclonal (rabbit) and several monoclonal antibodies to human VnR isolated from placenta were prepared. The polyclonal and a single monoclonal antibody, B6H12, bound to PMN as assessed by fluorescence flow cytometry analysis. The effects of these antibodies on cc-RGDS-stimulated ingestion were tested. As shown in FIGS. 3A and B, both antibodies inhibited cc-RGDS-stimulated ingestion in a dose-dependent manner with complete inhibition at approximately 4 µg/ml. This dose of either antibody had no effect on EIgG ingestion by buffer-treated PMN (FIGS. 3A and B); however, at concentrations of 16 µg/ml or greater, treatment of PMN with either antibody significantly stimulated ingestion in the absence of cc-RGDS. Three other monoclonal antibodies made to the VnR, (B3F12, 6H12, 3F12), did not bind to PMN and did not have any effect on either cc-RGDS-stimulated or non-stimulated ingestion of EIgG. Antibody to the VmR beta-chain, mAb 7G2 (Brown and Goodwin, supra.), which binds to platelets and can immunoprecipitate VnR from placenta and gp IIb/IIIa from platelets, was also tested. This mAb also did not bind to PMN and did not affect either cc-RGDS-stimulated or non-stimulated ingestion by PMN. PMI-1, an anti IIb mAb [Ginsberg, et al., *J. Clin. Invest.* 78, 1103–1111 (1986)], also does not bind to PMN (Brown and Goodwin, supra). In addition, neither polyclonal antibody to the fibronectin receptor (anti-VLA-5) [Brown and Juliano, *J. Cell Biol.* 103, 1595–1603 (1986)] nor mAb A-lA5 (anti-VLA beta chain) [Hemler et al., *J. Biol. Chem.* 262, 3300–3309 (1987)] had any effect on either cc-RGDS-stimulated or non-stimulated ingestion of EIgG. The effect of mAb B6H12 and Fab anti-VnR was specific for cc-RGDS-stimulated phagocytosis because neither antibody had any effect on EIgG ingestion stimulated by phorbol ester treatment of PMN (data not shown). These data suggest that B6H12 recognizes an antigen which, while it binds to the RGD sequence, is not VnR, gpIIb/IIIa or a VLA.

To assess if B6H12 and the Fab anti VnR prevented phagocytosis enhancement by inhibiting ligand binding, the binding of radiolabelled cc-RGDS to antibody-treated PMN was examined. As shown in Table 2, both mAb B6H12 and Fab anti-VnR reduced cc-RGDS binding by 93.8% and 95.7%, respectively. In contrast, mAb B3F12 reduced cc-RGDS binding only by 7.4%. These data indicate that the polyclonal and the monoclonal antibody B6H12 inhibited cc-RGDS-stimulated phagocytosis because they inhibited binding of the cc-RGDS ligand to the cell surface.

C. mAB B6H12 recognizes a cell-surface heterodimer distinct from previously described members of the receptor family.

In order to ascertain the structure of the receptor recoqnized by the Fab anti-VnR and mAb B6H12 and compare it to the structure of the receptor isoated by RGD affinity chromatoqraphy (Brown and Goodwin, supra), PMN was surface-labelled and immunoprecipitated with the polyclonal anti-VnR and several of the monoclonal antibodies produced against purified VnR from placenta. Both the polyclonal antibody and mAb B6H12 immunoprecipitate a heterodimer of 140 kd and 105 kd upon reduction (FIG. 4, lanes 2 and 4). However, neither mAb 7G2 (anti-gp IIb/IIIa) nor mAb B3F12 (anti-VnR) immunoprecipitated any detectable proteins from PMN. On the other hand, both mAb 7G2 and mAb B3F12 but not mAb B6H12 immunoprecipitated a heterodimer from iodinated placental membrane proteins of 130 kd and 100 kd upon reduction (data not shown). To further distinguish the B6H12 antigen from the gp IIb/IIIa antigen, surface-labelled platelets were immunoprecipitated with mAb 7G2 and the precipitate compared under non-reducing conditions to the mAb B6H12 immunoprecipitate from PMN (FIG. 5, lanes 2 and 3). As is readily apparent, these two antibodies immunoprecipitate heterodimers with completely distinct alpha and beta chain $M_r$. The PMN heterodimer cannot be immunoprecipitated with an antibody that recognizes the beta chain of the gp IIb-/IIIa-VnR family (mAb 7G2) and is therefore distinct from the cytoadhesin group of integrin receptors.

The possibility that the B6H12 antigen was a member of the LFA-1, Mac-1, p150,95 family of cell adhesion receptors was then investigated. As shown in FIG. 6, mAb B6H12 binds normally to PMN from a patient with leukocyte adhesion deficiency (LAD) [Anderson and Springer, *Ann. Rev. Medicine* 1987)] as assessed by FACS analysis. This patient has been found previously [Anderson et al., *J. Infect. Dis.* 152, 668–689 (1985)] to lack expression of all members of this family, and PMN from this patient fail to express any beta chain antigen as assessed by FACS analysis using antibody to the beta chain, mAb 1B4, [Wright et al., *Proc. Natl. Acad. Sci. U.S.A.* 89, 5699–5703 (1985)] (data not shown). In addition, binding of radiolabelled cc-RGDS was assessed on both normal and LAD PMN; normal PMN bound 11,978 RGDS-specific cpms/$10^6$ PMN while the LAD PMN bound 12,616 RGDS-specific cpms/$10^6$ PMN. Moreover, early work indicated that treatment of PMN lysates with mAb 1B4 did not immunoprecipitate the PMN receptor which bound to RGD-sepharose (Brown and Goodwin, supra). In concert, these data indicate that the B6H12 antigen is not a member of the LFA-1, Mac-1, p150,95 family of cell adhesion receptors and represents a previously unrecognized RGD-binding receptor on PMN.

D. Many RGDS-containing proteins stimulate PMN Fc receptor-mediated ingestion via a B6H12-dependent mechanism.

Because cc-RGDS but not cc-DGDS nor cc-C was able to augment PMN phagocytosis of EIgG significantly, it was concluded that the RGD(S) sequence was the ligand responsible for phagocytosis enhancement. This conclusion was substantiated by the fact that unlinked GRGDSC peptide inhibited specific cc-RGDS binding by 79.6% while an irrelevant peptide had no effect (Table 2). This inhibition was not limited to free RGDS peptide but could be demonstrated also by a protein containing an RGDS sequence, fibronectin (Fn), which inhibited specific cc-RGDS binding by 76.5%. These data suggested that the mAb B6H12 recognizes a receptor which can recognize the RGD sequence of many proteins.

Figure 7C:
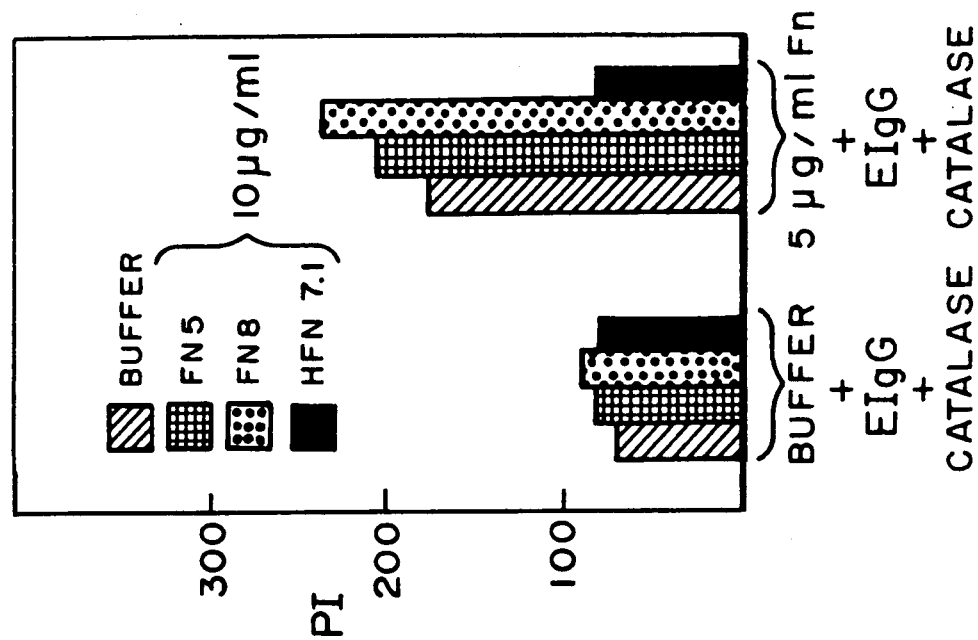
Figure 7B:
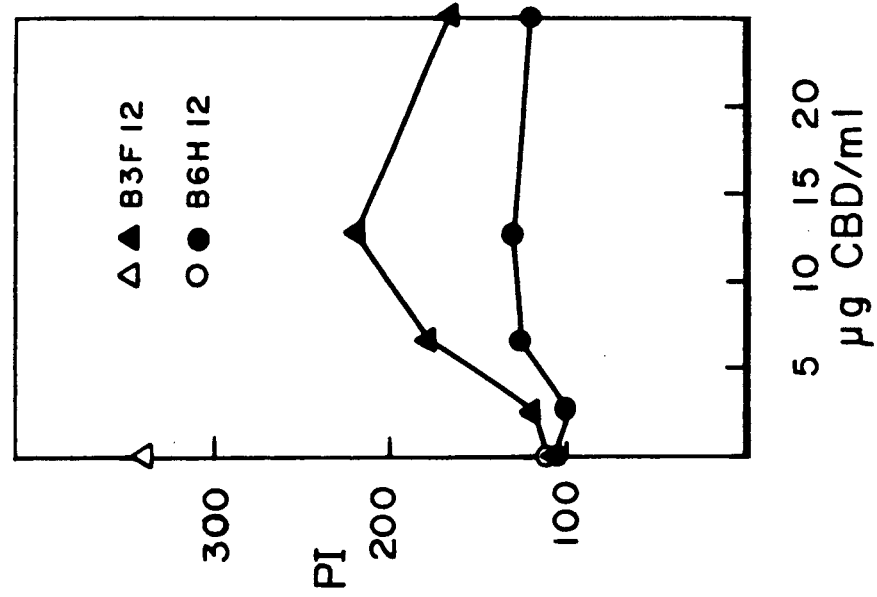
Figure 7A:
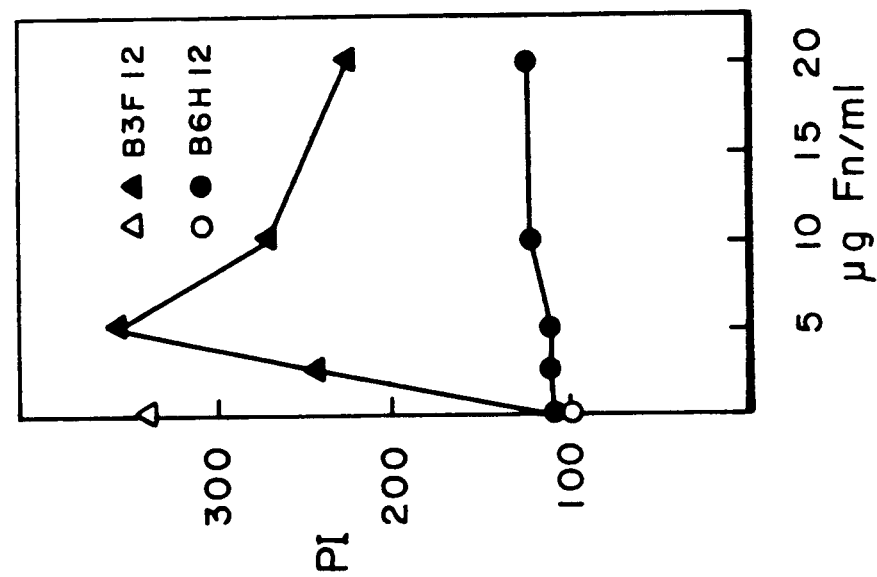

The effect of fibronectin (Fn) on PMN Fc receptor-mediated phagocytosis was examined and, as shown in FIG. 7A, Fn stimulated ingestion in a dose-dependent manner. As with cc-RGDS stimulation (FIG. 1A), the dose-response curve was biphasic. Fn-mediated augmentation of ingestion was completely abrogated by treatment of the PMN with mAb B6H12 but not mAb B3F12. However, non-stimulated or baseline levels of EIgG ingestion were never affected by mAb B6H12 treatment. The cell-binding domain of Fn (CBD) which contains the RGDS sequence also stimulated EIgG ingestion, though much less efficiently than the intact Fn molecule (FIG. 7B). This is in contrast to monocyte ingestion which is not augmented by the purified CBD fragment [Bohnsack et al., *J. Immunol.* 136, 3793-3798 (1986); Brown and Goodwin, supra]. However, mAb B6H12 and not mAb B3F12 completely abrogated CBD-stimulated ingestion (FIG. 7B). To further localize the region of the Fn molecule which was involved in phagocytosis enhancement, an optimal dose of Fn was incubated with various monoclonal antibodies which recognize distinct domains of Fn. As shown in FIG. 7C, neither Fn8, which recognizes the amino terminus of Fn, nor Fn5, which recognizes a site in the CBD carboxy terminal to the RGDS sequence, (Bohnsack et al., supra) had any effect on Fn-stimulated ingestion of EIgG. However, HFn7.1, which recognizes a site close to the RGDS sequence in the CBD, completely abrogated Fn-stimulated phagocytosis. A similar effect of HFn7.1 has been observed for Fn-stimulated monocyte phagocytosis (Bohnsack et al. supra). These data indicate that the CBD of the Fn molecule which contains the RGDS sequence was responsible for augmentation of PMN Fc receptor-mediated ingestion by intact Fn and that mAb B6H12 recognized the receptor which mediated this enhancement.

Figure 8A:
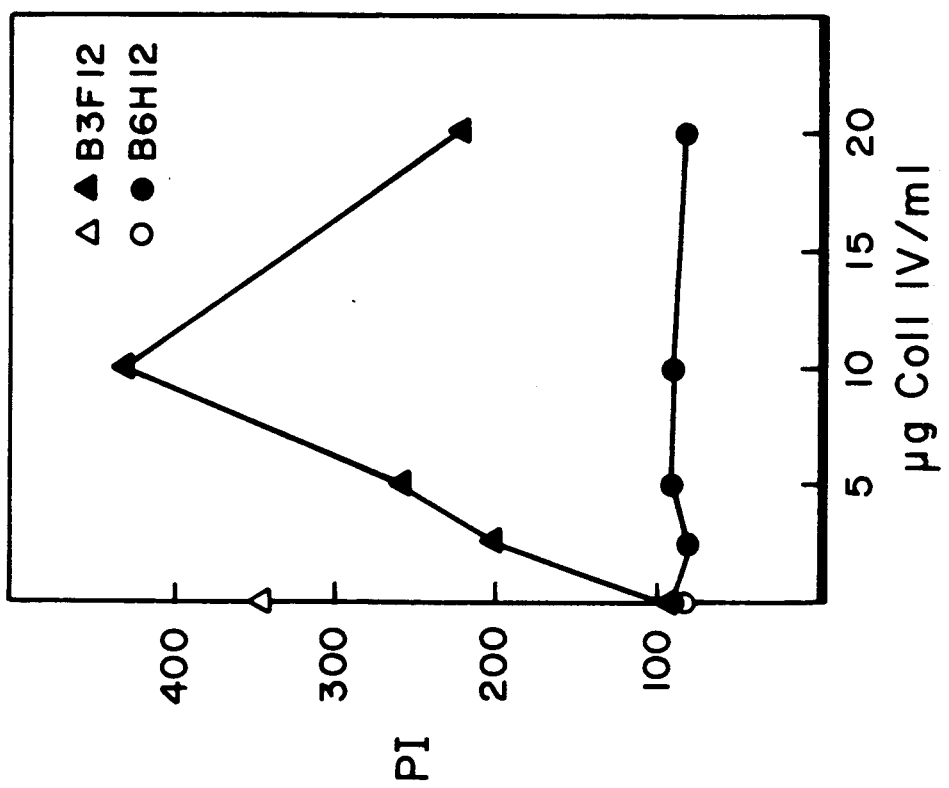

Other extracellular matrix proteins which have been reported to contain RGD sequences were investigated for their ability to augment ingestion via the B6H12 antigen. As shown in FIGS. 8A and B, both collagen type IV and laminin enhanced PMN Fc receptor-mediated ingestion; however, mAb B6H12 inhibited only collagen-stimulated ingestion and not laminin-stimulated ingestion. Therefore, the B6H12 antigen was not able to recognize an RGD sequence in all extracellular matrix proteins. This is not surprising for laminin, because it has been shown to interact with non-integrin receptors via domains completely distinct from the RGD sequence [Graf et al, *Cell* 48, 989-996 (1987)].

Because the B6H12 receptor appeared to recognize several proteins with RGD sequences, it appeared to function like the gpIIb/IIIa receptor of platelets which binds vitronectin, von Willebrand's factor, and fibrinogen, as well as Fn. These proteins were also investigated for augmentation of inestion via the B6H12 antigen. As shown in FIG. 8, all three of these ligands stimulated PMN ingestion of EIgG in a dose-dependent manner. Moreover, the stimulated ingestion by all of these ligands was prevented by treatment of the PMN with mAb B6H12 but not mAb B3F12. These data indicate that the B6H12 receptor recognizes RGD sequences in many proteins and mediated phagocytosis stimulation by various but not all adhesive proteins.

Various other examples will be apparent to the person skilled in the art after reading the present disclosure without departing from the spirit and scope of the invention. It is intended that all such examples be included within the scope of the appended claims.

What is claimed is:

1. Monoclonal antibody having the characteristics of B6H12, ATCC HB 9771.

* * * * *